US008636727B2

(12) United States Patent
Bissig et al.

(10) Patent No.: US 8,636,727 B2
(45) Date of Patent: Jan. 28, 2014

(54) PORTABLE IRRADIATING ARRANGEMENT

(75) Inventors: Alois Bissig, Flüelen (CH); Erich Zurfluh, Altdorf (CH)

(73) Assignee: Alplight (CH)

( * ) Notice: Subject to any disclaimer, the term of this patent is extended or adjusted under 35 U.S.C. 154(b) by 535 days.

(21) Appl. No.: 12/665,071

(22) PCT Filed: Apr. 30, 2008

(86) PCT No.: PCT/CH2008/000199
§ 371 (c)(1),
(2), (4) Date: Jan. 13, 2010

(87) PCT Pub. No.: WO2009/003295
PCT Pub. Date: Jan. 8, 2009

(65) Prior Publication Data
US 2010/0198201 A1 Aug. 5, 2010

(30) Foreign Application Priority Data

Jun. 29, 2007 (CH) .................................. 1051/07

(51) Int. Cl.
*A61B 18/18* (2006.01)
(52) U.S. Cl.
USPC .......................................................... 606/13
(58) Field of Classification Search
USPC .................... 607/100, 88, 89, 80; 606/13, 15
See application file for complete search history.

(56) References Cited

U.S. PATENT DOCUMENTS

| 4,622,967 A | 11/1986 | Schachar |
| 4,979,180 A | 12/1990 | Muncheryan |
| 5,150,704 A * | 9/1992 | Tatebayashi et al. ........... 607/89 |
| 5,304,172 A * | 4/1994 | Manoukian et al. ............ 606/15 |
| 5,360,426 A * | 11/1994 | Muller et al. ................... 606/13 |
| 5,401,171 A | 3/1995 | Paghdiwala |
| 5,464,436 A | 11/1995 | Smith |

(Continued)

FOREIGN PATENT DOCUMENTS

| EP | 0 586 353 | 3/1994 |
| EP | 1 384 446 | 1/2004 |

(Continued)

OTHER PUBLICATIONS

International Search Report in related application PCT/CH2008/000199, dated Oct. 16, 2008, with one page of English translation of relevant portion (9 pages total).

(Continued)

*Primary Examiner* — Jessica Stultz
*Assistant Examiner* — Tuan Nguyen
(74) *Attorney, Agent, or Firm* — Ostrolenk Faber LLP

(57) ABSTRACT

The present disclosure relates to a portable irradiating arrangement having a light source, particularly a laser diode, comprising an outer sleeve, an inner sleeve, and a radiation distributing probe, whereby the inner sleeve is mounted in the outer sleeve and the radiation distributing probe may be attached at a probe-facing end of the outer sleeve, whereby the irradiating arrangement is designed in such a way that the light source can be turned on only when the radiation distributing probe is attached to the outer sleeve. The invention relates further to a portable irradiating arrangement, in which the inner sleeve is in contact with the radiation distributing probe in such a way that the inner sleeve must be detached from the radiation distributing probe before removal of the radiation distributing probe from the outer sleeve.

17 Claims, 9 Drawing Sheets

(56) References Cited

U.S. PATENT DOCUMENTS

| | | | |
|---|---|---|---|
| 6,273,885 B1 | 8/2001 | Koop et al. | |
| 6,312,451 B1 | 11/2001 | Streeter | |
| 6,780,184 B2 * | 8/2004 | Tanrisever | 606/45 |
| 7,029,193 B1 | 4/2006 | Chao | |
| 7,100,615 B1 | 9/2006 | Kert | |
| 2005/0228385 A1 * | 10/2005 | Iott et al. | 606/61 |
| 2007/0027443 A1 | 2/2007 | Rose et al. | |
| 2007/0254349 A1 | 11/2007 | Vizethum et al. | |
| 2008/0051856 A1 * | 2/2008 | Vizethum et al. | 607/80 |

FOREIGN PATENT DOCUMENTS

| | | | |
|---|---|---|---|
| EP | 1 433 499 A | 6/2004 | |
| GB | 2 211 958 | 7/1989 | |
| JP | 1-99575 | 4/1989 | |
| JP | 07-323093 A | 12/1995 | |
| JP | 8-182687 | 7/1996 | |
| WO | WO 2004/105874 | 12/2004 | |
| WO | WO 2004105874 A2 * | 12/2004 | |
| WO | WO 2005/099757 | 10/2005 | |
| WO | WO 2006/047808 | 5/2006 | |
| WO | WO 2006047808 * | 5/2006 | A61B 18/22 |
| WO | WO 2007/005313 | 1/2007 | |

OTHER PUBLICATIONS

National Search Report for the Swiss priority application No. 1051/07, dated Oct. 31, 2007 (10 pages).
International Search Report dated Oct. 27, 2008, issued in corresponding international application No. PCT/CH2008/000199.

* cited by examiner

PORTABLE IRRADIATING ARRANGEMENT

CROSS REFERENCE TO RELATED APPLICATIONS

The present application is a 35 U.S.C. §371 National Phase conversion of PCT/CH2008/000199, filed Apr. 30, 2008, which claims benefit of Swiss Application No. 1051/07, filed Jun. 29, 2007, the disclosure of which is incorporated herein by reference. The PCT International Application was published in the German language.

BACKGROUND

The invention relates to a portable irradiating arrangement with a light source. A laser or a laser diode is preferably employed as the light source. An LED (light-emitting diode) or another white light source or an optical waveguide as well can be used, however. The portable laser arrangement can be used, for example, in the field of medical technology, particularly for the purpose of exposure to light, but it is not limited to applications in this field.

STATE OF THE ART

Irradiating arrangements are used in many ways in medical technology. Irradiating arrangements with a laser as the light source, so-called laser arrangements, are used, for example, in photodynamic therapy (PDT), photodynamic disinfection (PDD), and in low level light therapy (LLLT). Further, laser arrangements are also used for the cutting of tissue, drilling in or on teeth, for endodontic treatment, in veterinary medicine, for curing of dental fillings, for teeth whitening, and the like. It is advantageous for certain of the enumerated applications to use a portable laser arrangement.

Prior-art portable laser arrangements with optical powers in the range of more than 1 milliwatt to over 200 milliwatts are frequently designed so that the radiation can emerge unimpeded and can thus represent a danger to the user and the patient. Lasers of this type according to the laser classifications IEC 60825-1/IEC 601-2-22 or the corresponding ANSI standard(s) are assigned to laser class 3B or 4. Assigned to laser class 3B are laser arrangements whose accessible laser radiation is hazardous to the eyes and in special cases to the skin as well, diffuse scattered light not usually being hazardous. Assigned to laser class 4 are laser arrangements whose accessible laser radiation is highly hazardous for the eyes and hazardous for the skin; in this case, diffuse scattered light can also be hazardous and the laser radiation can cause a risk of fire or explosion. According to the aforementioned laser classifications, protective devices are to be provided for laser arrangements of these laser classes, such as, for example, a safety lock, a safety "interlock" connector, a "laser on" indicator, a "laser ready" indicator, redundant timer electronics, an "emergency stop" switch, etc. Furthermore, the user and patient must wear laser protection glasses, which at times can negatively affect the field of view; the cost of the laser protection glasses increases with the danger of the laser arrangement and thereby with the laser class. In prior-art laser arrangements of the aforementioned laser classes, additional, often cost-intensive protective devices are therefore necessary.

In many applications of laser arrangements, particularly in medical technology, contamination of the laser arrangement by blood, saliva, bacteria, tissue, etc., often occurs. Known laser arrangements from the prior art are often difficult to clean and to keep sterile. For example, such known laser arrangements may be sterilized in an autoclave with hot steam at 135° C.

DESCRIPTION OF THE INVENTION

The object of the present invention is to provide a portable irradiating arrangement having a light source, which in the case of a light source made as a laser or laser diode can be assigned to a lower or safer laser class than 3B. In particular, the portable irradiating arrangement of the invention in the case of a light source made as a laser or laser diode can be assigned to a laser class of 2M or a lower, safer laser class. In the case of laser class 2M, the accessible laser radiation is only within the visible range (400 nanometers to 700 nanometers). With a brief radiation duration (up to 0.25 seconds), it is also safe for the eyes as long as no optical instruments, such as loupes or magnifiers, are used.

It is a further object of the present invention to provide a portable irradiating arrangement that can be cleaned and sterilized simply and effectively.

Said object is achieved by means of the portable irradiating arrangement disclosed herein.

The portable irradiating arrangement of the invention comprises a light source, which is in particular a laser or a laser diode, an outer sleeve, an inner sleeve, and a radiation distributing probe, whereby the inner sleeve is mounted in the outer sleeve and the radiation distributing probe may be attached to one end of the outer sleeve. The end of the outer sleeve to which the radiation distributing probe is to be attached is also called the probe-facing end of the outer sleeve. The irradiating arrangement of the invention is designed in such a way that the light source may be turned on only when the radiation distributing probe is attached to the outer sleeve. In other words, the irradiating arrangement of the invention can be used by a user only when the radiation distributing probe is attached to the outer sleeve or to its probe-facing end. The light source can, of course, be a white light source, for example, an LED (light-emitting diode). Further, an optical waveguide, particularly an optical waveguide fiber, may also be used.

According to a preferred embodiment of the invention, a spring system is provided, which acts on the inner sleeve in the axial direction, so that a first section of the inner sleeve projects at least partially from the probe-facing end of the outer sleeve, whereby the radiation distributing probe is formed in such a way that in the attached state it presses or pushes back the part, projecting from the outer sleeve, of the first section of the inner sleeve against the spring pressure of the spring system at least partially into the outer sleeve.

A control element, particularly a push button or a touch panel, for turning on the light source is preferably provided on the outer sleeve and the inner sleeve preferably has an opening, whereby the axial distance between the control element and the opening is selected in such a way that the control element can be operationally connected via the opening with the light source only when the radiation distributing probe is attached.

In addition or alternatively, preferably a sensor that detects the attachment of the radiation distributing probe is provided in the outer sleeve.

It is assured in this way that the portable irradiating arrangement of the invention can be placed into operation or its light source can be turned on only with an attached radiation distributing probe. This results in a classification of the portable irradiating arrangement of the invention in a laser class provided for laser arrangements relatively safe for the user. If necessary, the provided protective devices can prove to be less expensive than in the laser arrangements known from the prior art in laser classes 3B and 4 or be totally omitted, so that the use of the portable irradiating arrangement of the invention is cost-effective.

According to another aspect of the invention, a portable irradiating arrangement is provided, which comprises a light source, which is in particular a laser or a laser diode or an optical waveguide, an outer sleeve, an inner sleeve, and a radiation distributing probe, whereby the inner sleeve is mounted in the outer sleeve and the radiation distributing probe is attached at one end of the outer sleeve, whereby the inner sleeve is in contact with the radiation distributing probe in such a way that the inner sleeve must be detached from the radiation distributing probe before removal of the radiation distributing probe from the outer sleeve. The inner sleeve in particular prevents the radiation distributing probe from being removed from the outer sleeve by rotation. In this embodiment as well, the light source can be formed as a white light source, for example, as an LED.

According to a preferred embodiment, the inner sleeve in a first, probe-facing section has an outer profile and the radiation distributing probe a matching inner profile, whereby the inner profile sits on the outer profile when the radiation distributing probe is attached. The outer profile of the inner sleeve is preferably made as a hexagonal head and the inner profile of the radiation distributing probe is preferably made as a matching hexagonal socket.

This has the advantage that the portable irradiating arrangement of the invention is easy to clean and sterilize. To this end, the outer sleeve can be cleaned and sterilized in a so-called autoclave. The inner sleeve, in which preferably the light source, a current supply for the light source, and electronic components for activating the light source are provided, is protected by the outer sleeve and the radiation distributing probe during the cleaning and sterilization process, because the radiation distributing probe can be removed only after removal of the inner sleeve from the outer sleeve. The extent to which the inner sleeve can be sterilized or autoclaved depends in particular on the design of its electronic components. If this is also necessary for safety reasons, then the inner sleeve can also be removed out of the outer sleeve before sterilization or autoclaving.

BRIEF DESCRIPTION OF THE DRAWINGS

Additional advantageous embodiments of the invention emerge from the dependent claims and the exemplary embodiments illustrated hereafter with use of the drawings. In the drawings:

In the figures, the same reference characters refer to structurally or functionally similarly acting components. The figures do not claim to be a to-scale illustration.

MEANS FOR IMPLEMENTING THE INVENTION

Figure 1:
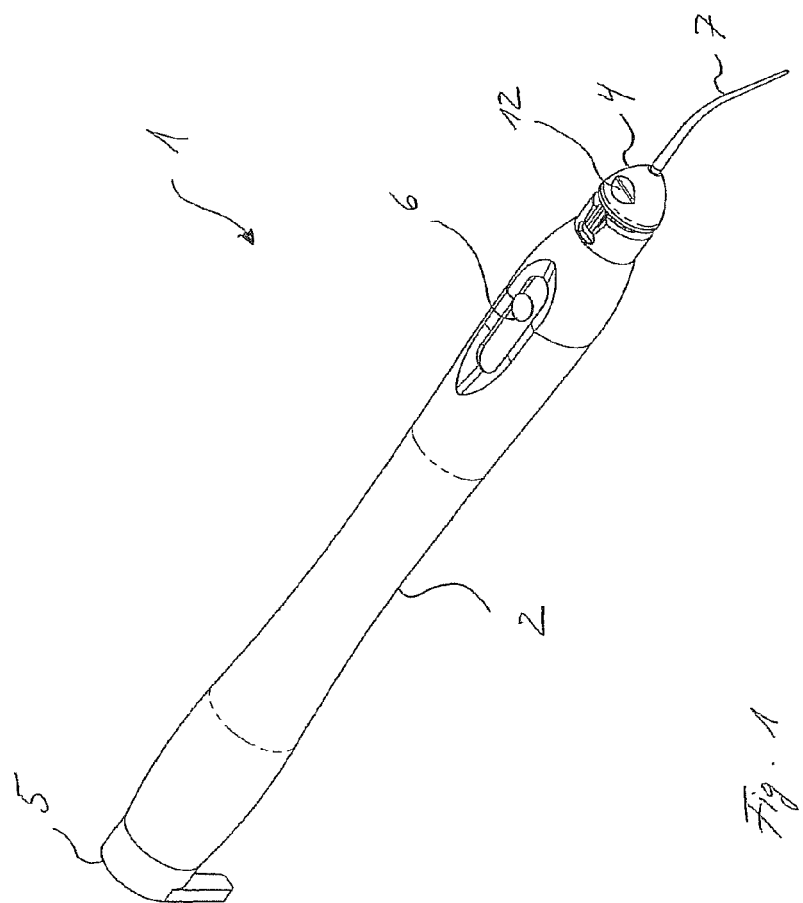
FIG. 1 shows an illustration of a portable irradiating arrangement of the invention.
Figure 2:
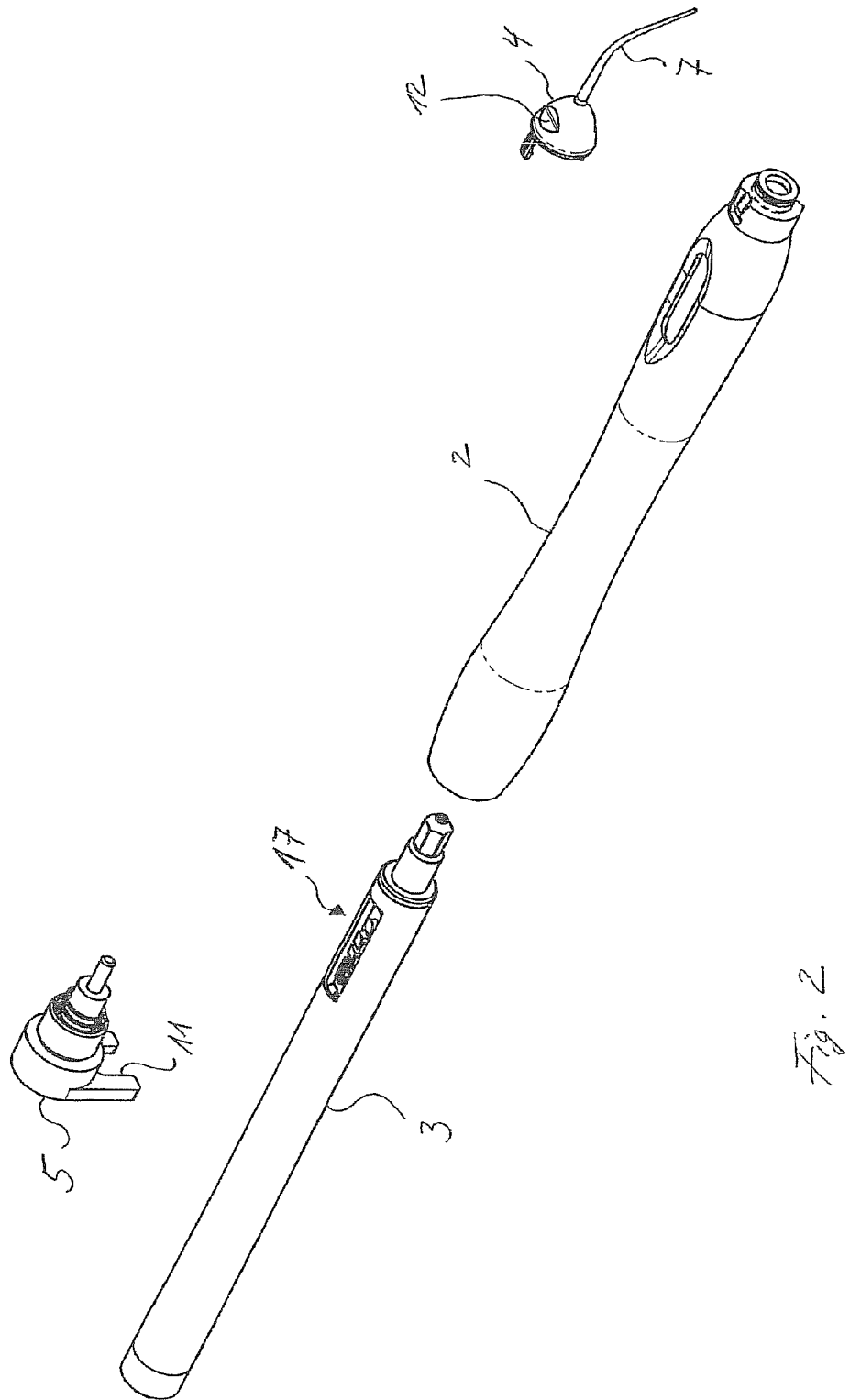
FIG. 2 shows an exploded view of the illustration in FIG. 1.

FIGS. 1 and 2 show a portable irradiating arrangement 1 of the invention in an assembled and exploded view. Portable irradiating arrangement 1 comprises an outer sleeve 2 and an inner sleeve 3, which is arranged removably in outer sleeve 2. A radiation distributing probe 4 is attached removably at one end of outer sleeve 2, particularly by means of a plug-in connection, whereby barbs (not shown) may be provided that break off upon rotation. It is also possible, of course, to attach radiation distributing probe 4 to outer sleeve 2 by means of a screw connection. This end of outer sleeve 2 is designated accordingly also as the probe-facing end of the outer sleeve. A closure device 5 is attached removably at the end of outer sleeve 2, said end that is opposite to said probe-facing end of the outer sleeve.

Figure 3:
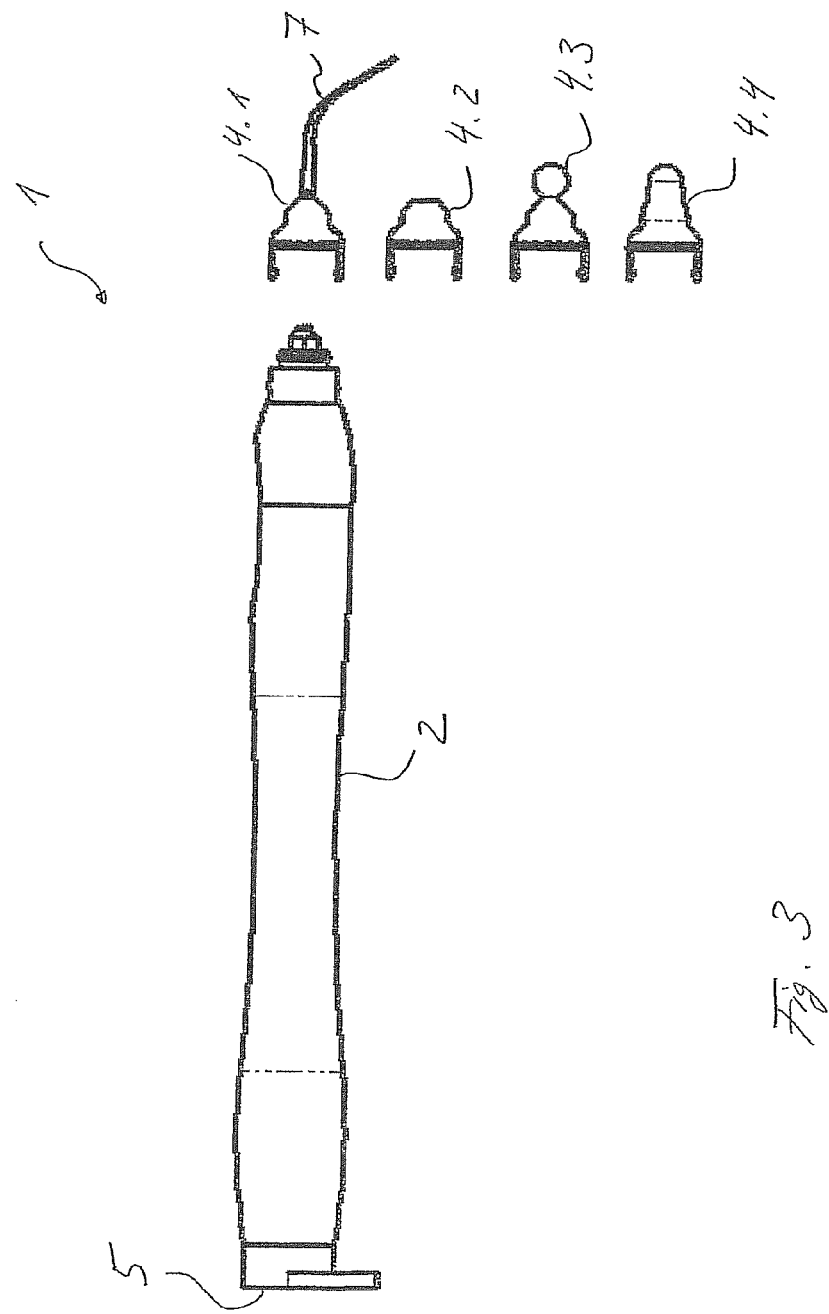
FIG. 3 shows a side view of a portable irradiating arrangement of the invention with various radiation distributing probes.

Radiation distributing probe 4 scatters or absorbs the radiation preferably in such a manner that the emerging radiation has a power density that is safe for the skin and eyesight of a user and a patient. Radiation distributing probe 4 may have a light guide 7 (also compare radiation distributing probe 4.1 in FIG. 3). Other possible embodiments of radiation distributing probe 4 are shown as radiation distributing probe 4.2, 4.3, and 4.4 in FIG. 3.

A control element 6 for turning on a light source 14, preferably arranged in inner sleeve 3 of portable irradiating arrangement 1, (compare FIGS. 6, 7, and 9) is provided, which is preferably made as a push button, touch panel, switch, and/or button. In addition or alternatively, control element 6 can be formed as acting capacitively, inductively, and/or optically. Control element 6 is preferably arranged in or on outer sleeve 2. Control element 6 can also be made as a remote control at a distance from irradiating arrangement 1, e.g., as a foot-operated switch, which during actuation transmits a suitable signal to electronic components 15 of irradiating arrangement 1, for example, via radio, ultrasound, and/or by means of infrared.

Figure 6:
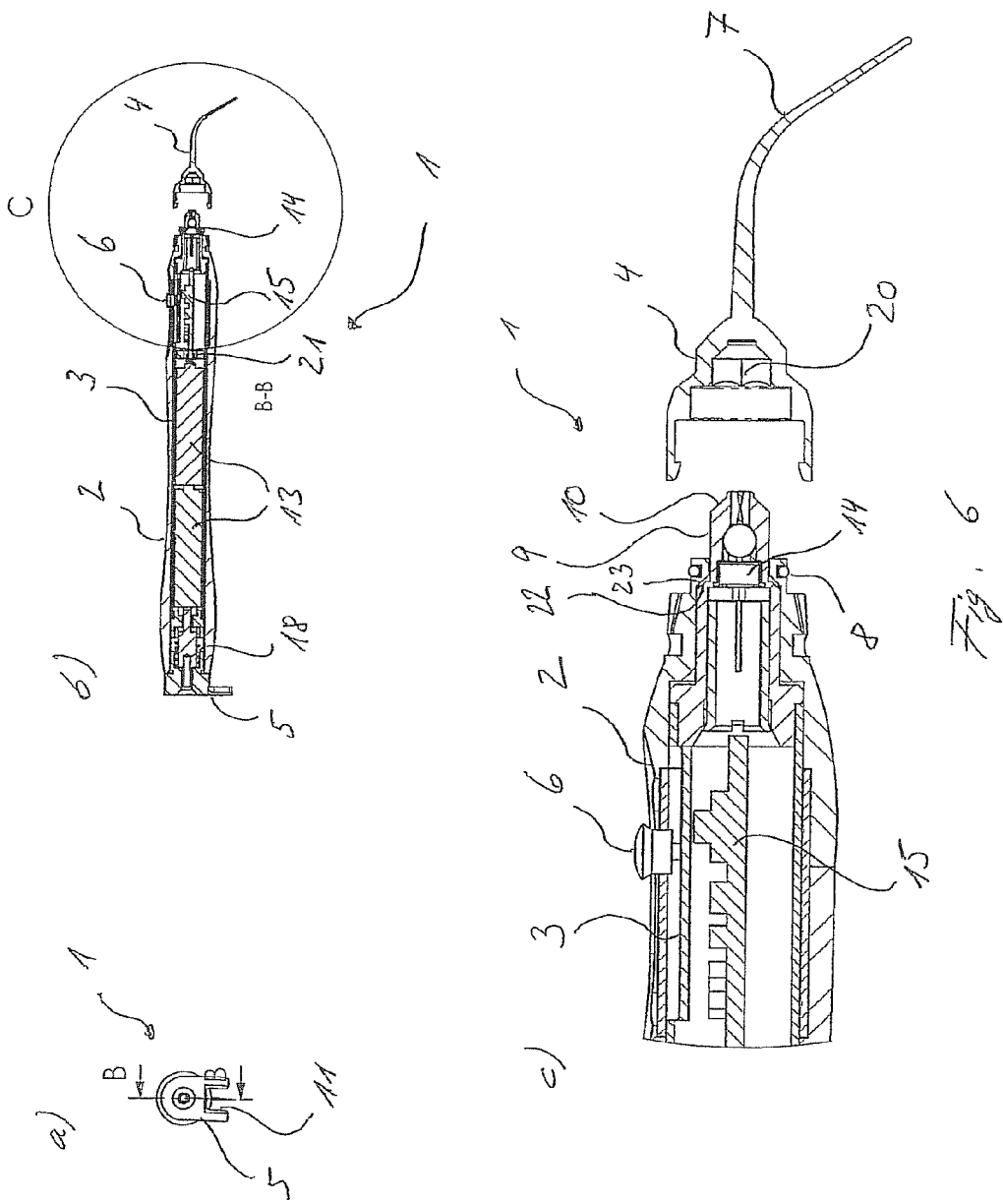
FIGS. 6 and 7 show an illustration of an exemplary embodiment of a portable irradiating arrangement of the invention in a back view (FIG. 6a), as a cross section with a removed radiation distributing probe (FIG. 6b), as a detail with a removed radiation distributing probe (FIG. 6c), and as a detail with an attached radiation distributing probe (FIG. 7)
Figure 7:
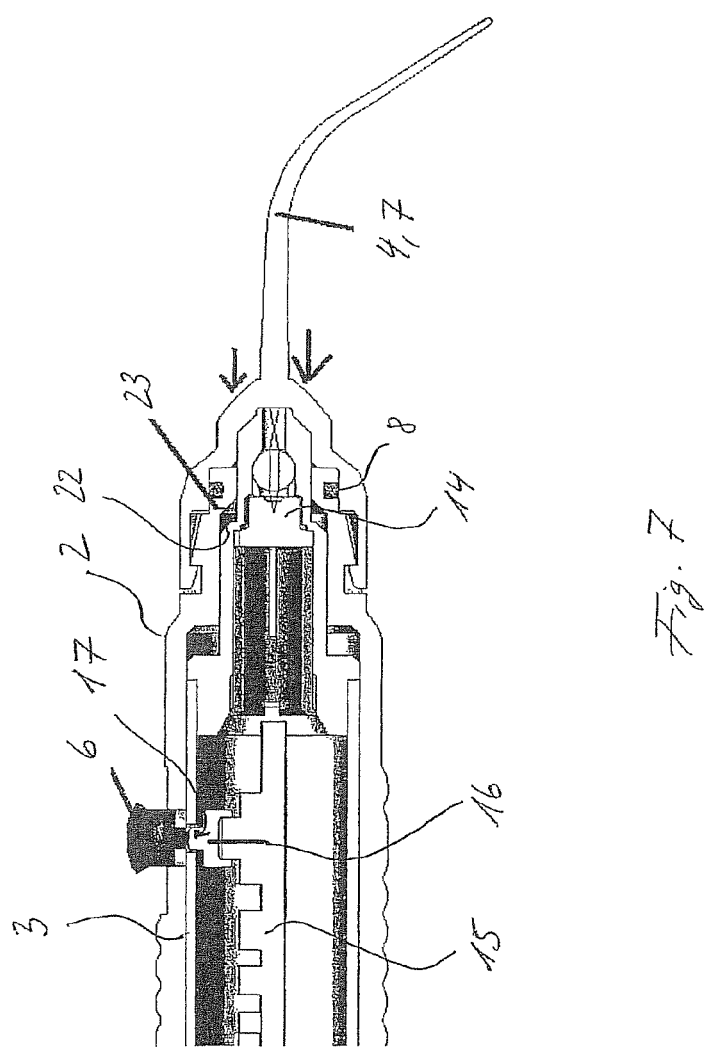
Figure 9:
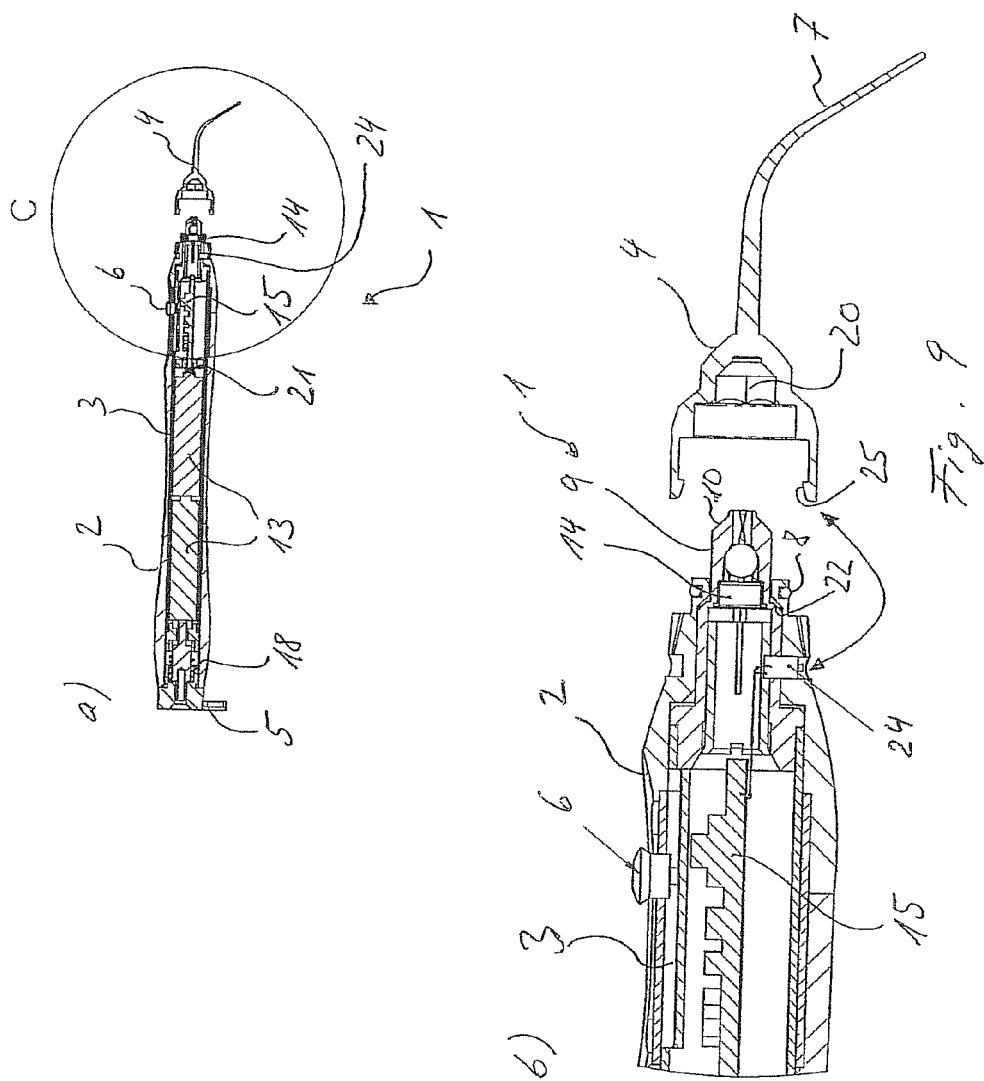
FIG. 9 shows a cross section of another exemplary embodiment of a portable irradiating arrangement of the invention with a removed radiation distributing probe (FIG. 9a) and a detail thereof (FIG. 9b).

Inner sleeve 3 has an opening 17, whereby with an attached radiation distributing probe 4 control element 6 can be operationally connected via opening 17 with light source 14 arranged in inner sleeve 3 (compare FIGS. 6, 7, and 9). Light source 14 or portable irradiating arrangement 1 can then be turned on by actuating control element 6.

Figure 4:
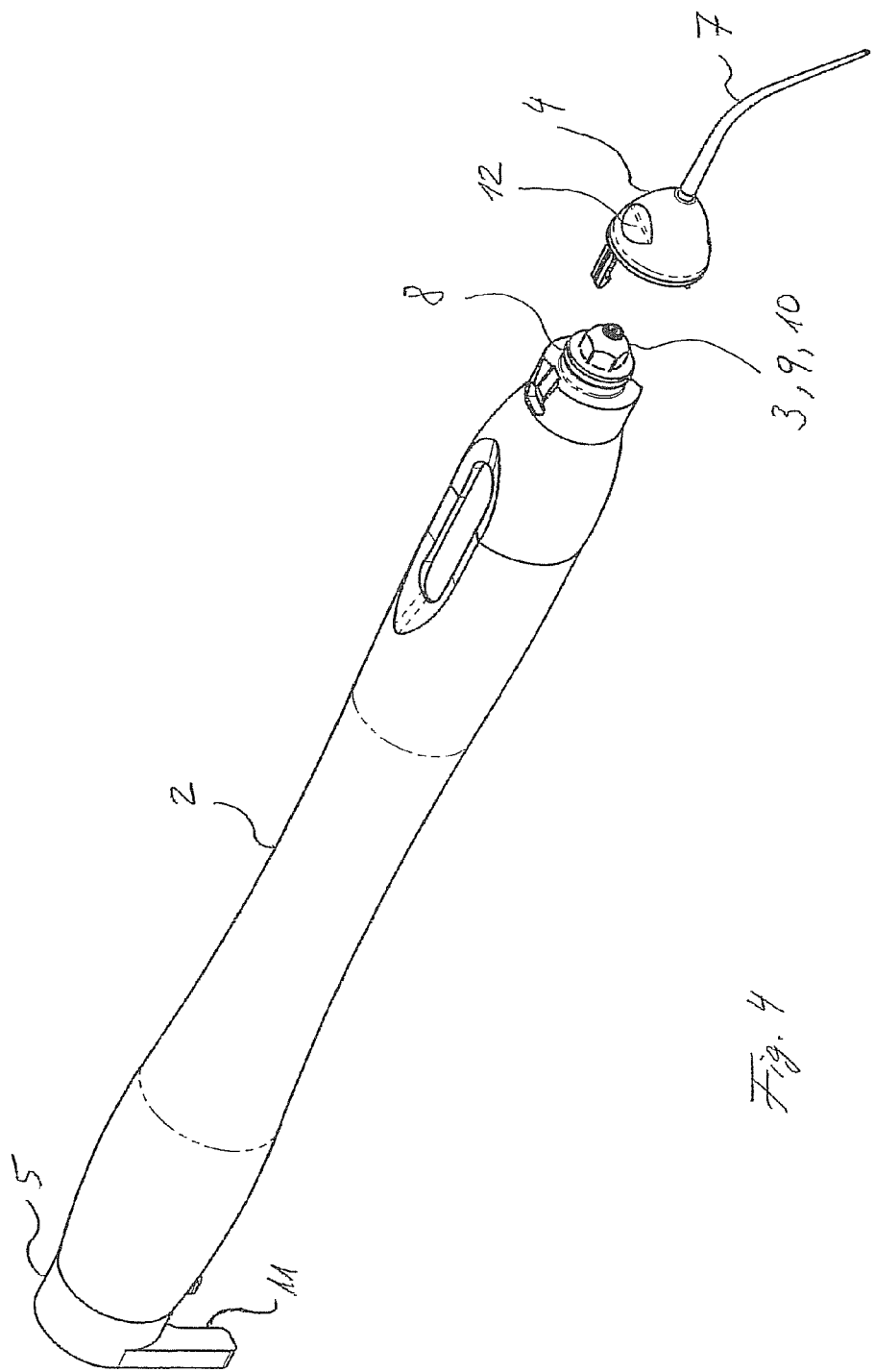
FIG. 4 shows an illustration of a portable irradiating arrangement of the invention with a removed radiation distributing probe.

Inner sleeve 3 is mounted rotation-resistant in outer sleeve 2, preferably by means of closure device 5. As shown in FIG. 4, inner sleeve 3 with a first, probe-facing section 9 at the probe-facing end of outer sleeve 2 projects from said outer sleeve. An outer profile 10, which is preferably formed as a hexagonal head, is provided at least on a part of said first, probe-facing section 9 at its periphery. Radiation distributing probe 4 has an inner profile 20 matching said outer profile 10 (compare FIGS. 6c and 9b), so that inner profile 20 in the case of an attached radiation distributing probe 4 sits on outer profile 10 of first section 9 of inner sleeve 3. If outer profile 10 of inner sleeve 3 is made as shown as a hexagonal head, then inner profile 20 (compare FIGS. 6c and 9b) of radiation distributing probe 4 is made as a hexagonal socket matching said hexagonal head.

The provision of an outer profile 10 on a first section 9 of inner sleeve 3 and a matching inner profile 20 on radiation distributing probe 4 represents an anti-rotation protection. As long as inner sleeve 3 is connected via its outer profile 10 to radiation distributing probe 4 or its inner profile 20, radiation distributing probe 4 cannot be removed from outer sleeve 2 by rotation. Before the removal of radiation distributing probe 4 from outer sleeve 2, therefore, inner sleeve 3 must first be detached from radiation distributing probe 4; i.e., outer profile 10 of inner sleeve 3 must be detached from inner profile 20 of radiation distributing probe 4. To this end, closure device 5, which is preferably connected via a plug-in and/or screw connection with outer sleeve 2, is detached from outer sleeve 2 and inner sleeve 3 is removed from outer sleeve 2. Radiation distributing probe 4 can then be detached from outer sleeve 2, particularly by a rotatory motion.

Figure 8:
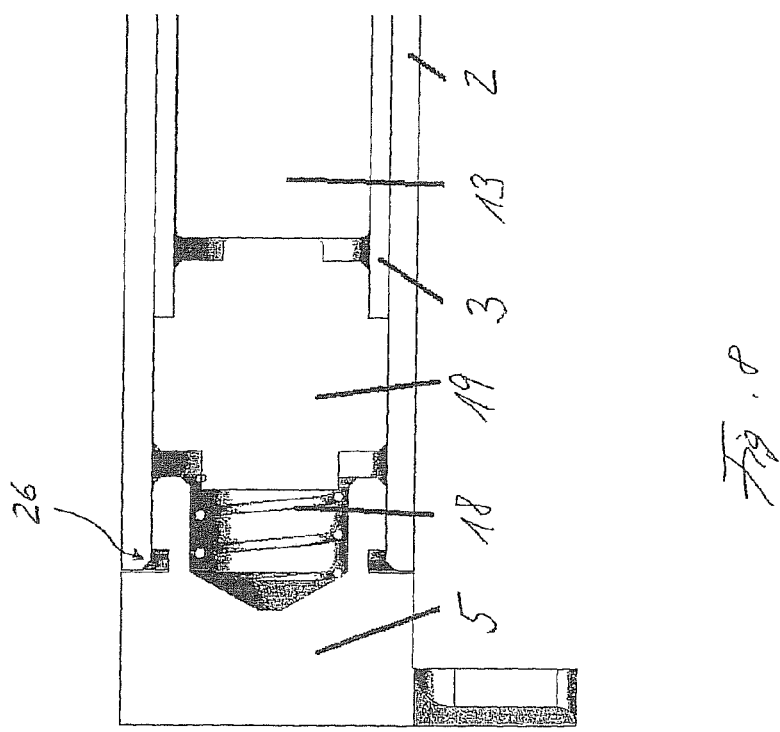
FIG. 8 shows a detail of a portable irradiating arrangement of the invention with a closure device at its back end.

Preferably, a sealing ring 8, which can be called a retaining ring, is provided in the area of outer sleeve 2, to which radiation distributing probe 4 is attached, to protect inner sleeve 3 from soiling. Of course, sealing ring 8 or an additional sealing ring or retaining ring may also be disposed in radiation distributing probe 4 itself. Another sealing ring 26 is preferably provided between closure device 5 and outer sleeve 2 (cf. FIG. 8).

The anti-rotation protection between inner sleeve 3 and radiation distributing probe 4 assures that radiation distributing probe 4 is not taken off outer sleeve 2 before the removal of inner sleeve 3 from outer sleeve 2. It is guaranteed in this way that during cleaning and sterilization of portable irradiating arrangement 1, inner sleeve 3, if it is sterilizable, does not come into contact with steam and/or other cleaning agents, because inner sleeve 3 preferably contains the light source, current supply for the light source, and other electronic components for controlling the light source. The inner sleeve is protected still further from soiling by sealing ring 8.

Figure 5:
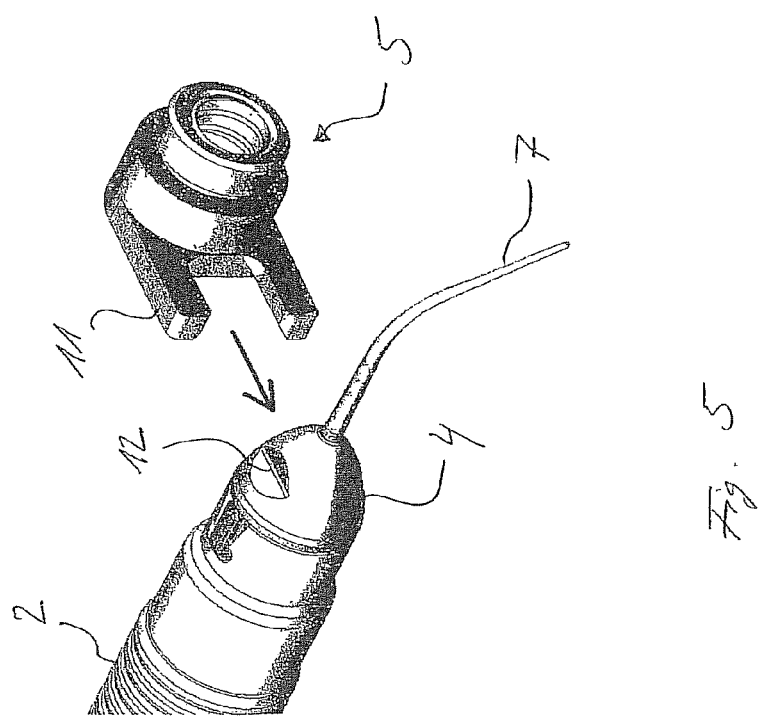
FIG. 5 shows an illustration of a closure device, having a release device, of the portable irradiating arrangement of the invention for the detachment of the radiation distributing probe.

Closure device 5 preferably has a release device 11 to release radiation distributing probe 4 from outer sleeve 2. As shown in FIG. 5, release device 11 is preferably made U-shaped. Further, radiation distributing probe 4 on its exterior preferably has a longitudinal projection 12, which is formed in such a way that release device 11 can engage in it to release radiation distributing device 4. In other words, U-shaped release device 11 is placed in or at longitudinal projection 12. Radiation distributing probe 4 can then be released or "twisted off" from outer sleeve 2 by rotation of closure device 5. In addition, by means of this design of release device 11, an unintentional rolling of irradiating arrangement 1 of the invention on or off a surface, for example, on or off a table, can be prevented and irradiating arrangement 1 can therefore be protected from damage.

FIGS. 6 to 9 show cross-sectional views and a back view of portable irradiating arrangement 1 of the invention, whereby in FIG. 6a the back view shows closure device 5 with U-shaped release device 11.

Light source 14, which is preferably a laser diode, which is preferably assigned a lens, is preferably arranged on the probe-facing side in inner sleeve 3. For the current supply for light source 14, a current source 13, which is preferably a battery or an accumulator, preferably two batteries or accumulators, is arranged in inner sleeve 3. Further, electronic components 15 for controlling or activating light source 14 are provided, which are preferably arranged in the axial direction between current source 13 and light source 14. Electrical components 15 have a contact 16 for control element 6.

An opening 17 (compare FIG. 2), via which the control element 6 can come into contact with or be operationally connected with contact 16 and in this way with electronic components 15, when radiation distributing probe 4 is attached to outer sleeve 2, is provided in inner sleeve 3. Contact 16 is preferably made as a button and control element 6 is preferably made as a push button, so that when control element 6 is pressed button 16 is pressed and in this way an electric circuit for the current supply for light source 14 is closed and light source 14 is supplied with current.

A spring system 18 for the spring mounting of inner sleeve 3 is provided. Spring system 18 is preferably provided between closure device 5 and inner sleeve 3 in the axial direction and made as a spring, whereby in addition a sealing plug 19 is arranged removably between spring system 18 and inner sleeve 3 for the independent closing of the end of inner sleeve 3, said end being opposite to radiation distributing probe 4 (compare FIG. 8). Of course, inner sleeve 3 can also be closed removably in another manner, so that current source 13 can be replaced if necessary. A spring system 21, particularly a spring, is likewise preferably provided between current source 13 and electronic components 15, to improve the electrical contact between current source 13 and electronic components 15.

An optical waveguide fiber (not shown) may also be used as light source 14, whereby in this case current source 13 and electronic components 15 can be omitted. Irradiating arrangement 1 is then formed as a fiber-optic handpiece, in which only outer sleeve 2 must be sterilized and not its interior.

FIG. 6c shows the detail labeled with "C" in FIG. 6b in an enlarged view. Radiation distributing probe 4 is shown separately, i.e., not attached to outer sleeve 2. Inner sleeve 3 is positioned by spring system 18 in outer sleeve 2 in such a way that the first, probe-facing section 9 projects at least partially from the probe-facing end of the outer sleeve. A second section 22 with a larger outer radius, which widens particularly in a conical manner, preferably adjoins first section 9 of inner sleeve 3. Outer sleeve 2 preferably has a stop 23 on its inner side for second section 22 of inner sleeve 3. Second section 22 of inner sleeve 3 is pressed against stop 23 of outer sleeve 2 by spring system 18, when radiation distributing probe 4 is not mounted on outer sleeve 2. In this position of inner sleeve 3 relative to outer sleeve 2, control element 6 is spaced so far apart or at a distance from opening 17 in inner sleeve 3 in the axial direction (compare FIGS. 2 and 7) that it cannot be operationally connected via opening 17 with electronic components 15 or their contact 16.

If radiation distributing probe 4 is now placed on outer sleeve 2, it moves back first section 9 of inner sleeve 3, at least partially against the spring pressure of spring system 18, into outer sleeve 2, so that second section 22 of inner sleeve 3 no longer lies against stop 23 of outer sleeve 2 and control element 6 is now located over opening 17 of inner sleeve 3 and thereby by its actuation can be operationally connected with electronic components 15 or their contact 16 (compare FIG. 7). The arrows in FIG. 7 indicate the direction of movement of radiation distributing probe 4 during attachment to outer sleeve 2 of portable irradiating arrangement 1.

If radiation distributing probe 4 is not attached to outer sleeve 2, inner sleeve 3 blocks control element 6, so that it can no longer be actuated, because opening 17 of inner sleeve 3 is no longer located under control element 6. Portable irradiating arrangement 1 can therefore not be operated without the attached radiation distributing probe 4 and in the case in which radiation distributing probe 4 is not attached, no radiation can emerge, so that safe use of portable irradiating arrangement 1 is assured.

FIGS. 9a and 9b show the irradiating arrangement illustrated in FIGS. 6b and 6c, whereby in addition a sensor 24 is provided, which is arranged in particular in or on outer sleeve 2. Sensor 24 is formed in such a way that it detects whether a radiation distributing probe 4 is attached to outer sleeve 2. It is connected via electrical lines, not described in greater detail, to electrical components 15. Sensor 24 is preferably formed as a pressure sensor, particularly as a button. If sensor 24 detects the attachment of a radiation distributing probe 4, it emits a corresponding signal or changes its position in such a way, if it is formed as a switch or button, that as a result of this the electrical circuit between current source 13 and light source 14 is closed when control element 6 is actuated and thereby portable irradiating arrangement 1 can be turned on by actuating control element 6.

If sensor 24 is made as a pressure sensor, radiation distributing probe 4 preferably has a projection 25, which presses on sensor 24, when radiation distributing probe 4 is placed on outer sleeve 2. In the case of sensor 24, this results in the detection of the attached radiation distributing probe 4. Sensor 24 is preferably arranged at the periphery of outer sleeve 2. Alternatively or in addition, the sensor 24 can also be arranged on the front side of outer sleeve 2. Particularly in the last case, a projection 25 on radiation distributing probe 4 is not absolutely necessary.

Of course, for safe operation of portable irradiating arrangement 1 of the invention, only one sensor 24 may also be provided, which is formed as described heretofore. In other words, it can be basically ignored that when radiation distributing probe 4 is not attached inner sleeve 3 projects further from outer sleeve 2 than with an attached radiation distributing probe 4, so that when radiation distributing probe 4 is not attached control element 6 cannot be operationally connected via opening 17 with electrical components 15, because it is already assured via sensor 24 that a current flow from current source 13 to light source 14 is possible only with an attached radiation distributing probe 4.

The embodiment according to FIG. 9 assures greater safety for the user, however, because only with the attachment of radiation distributing probe 4 is inner sleeve 3 pushed back so far into outer sleeve 2 that when actuation occurs via opening 17, control element 6 can be operationally connected with light source 14 and still in addition the attachment of radiation distributing probe 4 is detected via sensor 24.

Whereas preferred embodiments of the invention are described in the present application, it is obvious to point out that the invention is not limited to these and can be carried out in another manner as well within the scope of the following claims.

What is claimed is:

1. A portable irradiating arrangement having a light source, the portable irradiating arrangement comprising:
    an outer sleeve,
    an inner sleeve,
    a control element provided on the outer sleeve and configured for turning on the light source,
    a spring system which acts on the inner sleeve in an axial direction, and
    a radiation distributing probe, wherein
    the inner sleeve has an opening to allow the control element to be operationally connected to the light source through the opening, the inner sleeve is mounted in the outer sleeve, and the radiation distributing probe is attachable at a probe-facing end of the outer sleeve, and
    the spring system acts to displace the inner sleeve, when the radiation distributing probe is not attached to the outer sleeve, so that the control element is not operationally connected to the light source through the opening, and the attachment of the radiation distributing probe to the outer sleeve displaces the inner sleeve against the force of the spring system so that the control element is operationally connected to the light source through the opening, whereby the light source may be turned on only when the radiation distributing probe is attached to the outer sleeve.

2. The portable irradiating arrangement according to claim 1, wherein the spring system acts on the inner sleeve in the axial direction, so that a first section of the inner sleeve projects at least partially from the probe-facing end of the outer sleeve, and
    the radiation distributing probe is configured such that in the attached state, it presses a part, projecting from the outer sleeve, of the first section of the inner sleeve, against the spring pressure of the spring system, at least partially into the outer sleeve.

3. The portable irradiating arrangement according to claim 2, wherein the inner sleeve includes a second section, with a larger outer radius than the first section of the inner sleeve, particularly a conically widening section, that adjoins the first section of the inner sleeve, and
    the outer sleeve has a stop for the second section of the inner sleeve, and
    when the radiation distributing probe is removed, the spring system presses the second section of the inner sleeve against the stop of the outer sleeve.

4. The portable irradiating arrangement according to claim 1, wherein
    the opening of the inner sleeve is positioned such that the axial distance between the control element and the opening is selected to allow the control element to be operationally connected via the opening with the light source only when the radiation distributing probe is attached to the outer sleeve.

5. The portable irradiating arrangement according to claim 1, wherein the control element is formed as a remote control.

6. The portable irradiating arrangement according to claim 5, wherein the remote control is a foot-operated switch.

7. The portable irradiating arrangement according to claim 1, wherein the control element is formed capacitively, inductively, and/or optically and is selected from a group consisting of a push button, a touch panel, a switch, and a button.

8. The portable irradiating arrangement according to claim 1, further comprising a sensor configured to detect the attachment of the radiation distributing probe and provided in or on the outer sleeve.

9. The portable irradiating arrangement according to claim 1, wherein the inner sleeve is connected to the radiation distributing probe such that the inner sleeve must, be detached from the radiation distributing probe before removal of the radiation distributing probe from the outer sleeve.

10. The portable irradiating arrangement according to claim 1, wherein the inner sleeve is mounted in the outer sleeve in a rotation resistant manner.

11. The portable irradiating arrangement according to claim 1, wherein the inner sleeve includes a first, probe-facing section that has an outer profile and the radiation distributing probe includes a matching inner profile, whereby the inner profile of the radiation distribution probe sits on the outer profile of the inner sleeve when the radiation distributing probe is attached.

12. The portable irradiating arrangement according to claim 11, wherein the outer profile of the inner sleeve is made as a hexagonal head and the inner profile of the radiation distributing probe is made as a matching hexagonal socket.

13. The portable irradiating arrangement according to claim 1, further comprising a closure device positioned at the end opposite to the probe-facing end of the outer sleeve, the closure device including a release device to release the radiation distributing probe from the outer sleeve.

14. The portable irradiating arrangement according to claim 13, wherein the release device is U-shaped and the radiation distributing probe has a longitudinal projection on its exterior, configured such that the release device engages in it to release the radiation distributing probe.

15. The portable irradiating arrangement according to claim 13, wherein the release device is configured to prevent rolling of the portable irradiating arrangement on or off a surface.

16. The portable irradiating arrangement according to claim 1, wherein the light source is an optical waveguide.

17. A portable irradiating arrangement according to claim 1, wherein the light source is a laser or laser diode which is in a laser class of 2M or in a lower, safer laser class under International Standard IEC 60825-1.

* * * * *

UNITED STATES PATENT AND TRADEMARK OFFICE
CERTIFICATE OF CORRECTION

PATENT NO. : 8,636,727 B2  Page 1 of 1
APPLICATION NO. : 12/665071
DATED : January 28, 2014
INVENTOR(S) : Bissig et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 682 days.

Signed and Sealed this

Twenty-second Day of September, 2015

Michelle K. Lee
*Director of the United States Patent and Trademark Office*